United States Patent
Kho et al.

(10) Patent No.: US 11,620,671 B2
(45) Date of Patent: Apr. 4, 2023

(54) METHOD AND SYSTEM FOR MANAGING MEDICAL INFORMATION PLATFORM BY USING BLOCKCHAIN, AND NON-TRANSITORY COMPUTER-READABLE RECORDING MEDIUM

(71) Applicant: MediBloc Co., Ltd., Seoul (KR)

(72) Inventors: Woo Kyun Kho, Seoul (KR); Eun Sol Lee, Seoul (KR)

(73) Assignee: MediBloc Co., Ltd., Seoul (KR)

( * ) Notice: Subject to any disclaimer, the term of this patent is extended or adjusted under 35 U.S.C. 154(b) by 88 days.

(21) Appl. No.: 17/045,569

(22) PCT Filed: Apr. 10, 2018

(86) PCT No.: PCT/KR2018/004217
§ 371 (c)(1),
(2) Date: Dec. 22, 2020

(87) PCT Pub. No.: WO2019/198839
PCT Pub. Date: Oct. 17, 2019

(65) Prior Publication Data
US 2021/0118005 A1    Apr. 22, 2021

(51) Int. Cl.
*G06Q 30/02*       (2023.01)
*G06Q 30/0226*   (2023.01)
(Continued)

(52) U.S. Cl.
CPC ......... *G06Q 30/0233* (2013.01); *G06Q 20/38* (2013.01); *G16H 15/00* (2018.01);
(Continued)

(58) Field of Classification Search
CPC .... G06Q 30/0233; G06Q 20/38; G06Q 20/06; G06Q 30/02; G06Q 30/0207–30/0277;
(Continued)

(56) References Cited

U.S. PATENT DOCUMENTS 7,885,413 B2 *   2/2011   Vasic ............... H04L 9/3271
                                                              380/282
10,231,077 B2 *  3/2019   Raduchel ............. G16H 10/60
(Continued)

FOREIGN PATENT DOCUMENTS

KR        101116230 B1        3/2012
KR    10-1591244 B1 *      2/2016
(Continued)

OTHER PUBLICATIONS

International Search Report of PCT/KR2018/004217 dated Jan. 11, 2019.

*Primary Examiner* — Thuy N Nguyen
(74) *Attorney, Agent, or Firm* — Dinsmore & Shohl LLP; Yongsok Choi, Esq.

(57) ABSTRACT

According to one aspect of the present invention, there is provided a method for managing a medical information platform using a blockchain, the method comprising the steps of: dynamically calculating an exchange ratio between tokens and points, with reference to at least one of an amount of points that a user intends to exchange for tokens on a medical information platform, an amount of tokens that the user intends to exchange for points on the medical information platform, an amount of tokens present in a token pool managed by the medical information platform, and an amount of points previously exchanged for tokens on the medical information platform; and providing the user with the tokens or points exchanged with reference to the calculated exchange ratio.

11 Claims, 4 Drawing Sheets

(51) Int. Cl.
*G16H 15/00* (2018.01)
*H04L 9/06* (2006.01)
*H04L 9/08* (2006.01)
*G06Q 20/38* (2012.01)
*H04L 9/00* (2022.01)

(52) U.S. Cl.
CPC .......... *H04L 9/0618* (2013.01); *H04L 9/0852* (2013.01); *H04L 9/50* (2022.05); *H04L 2209/56* (2013.01)

(58) Field of Classification Search
CPC ........ G16H 15/00; G16H 10/60; G16H 40/20; G16H 50/70; H04L 9/0618; H04L 9/0852; H04L 2209/38; H04L 2209/56; H04L 9/3239
See application file for complete search history.

(56) References Cited

U.S. PATENT DOCUMENTS

| | | | | |
|---|---|---|---|---|
| 2003/0177101 A1* | 9/2003 | Ferris | G06Q 20/06 | 705/65 |
| 2008/0270240 A1* | 10/2008 | Chu | G06Q 30/0239 | 434/350 |
| 2008/0301445 A1* | 12/2008 | Vasic | G06F 16/10 | 713/171 |
| 2009/0154776 A1* | 6/2009 | Mott | G01N 21/75 | 382/110 |
| 2011/0202402 A1* | 8/2011 | Fowler | G06Q 30/02 | 705/14.27 |
| 2012/0035948 A1* | 2/2012 | Borton | G16H 80/00 | 705/2 |
| 2015/0088754 A1* | 3/2015 | Kirsch | G06Q 20/401 | 713/171 |
| 2015/0106273 A1* | 4/2015 | Duma | G16H 10/65 | 705/51 |
| 2015/0180867 A1* | 6/2015 | Perez | H04L 63/0807 | 726/6 |
| 2016/0005014 A1* | 1/2016 | Shea | G06Q 20/102 | 705/39 |
| 2016/0148173 A1* | 5/2016 | Kelley | G06Q 20/20 | 705/16 |
| 2017/0017978 A1* | 1/2017 | Wallace | G06Q 30/0207 | |
| 2017/0140408 A1* | 5/2017 | Wuehler | G06Q 30/0207 | |
| 2017/0161439 A1* | 6/2017 | Raduchel | H04W 12/06 | |
| 2017/0228371 A1* | 8/2017 | Seger, II | G06F 21/64 | |
| 2017/0235970 A1* | 8/2017 | Conner | G06F 16/2358 | 707/690 |
| 2017/0337332 A1* | 11/2017 | Duma | G16H 10/65 | |
| 2017/0364999 A1* | 12/2017 | Herriger | G07F 17/32 | |
| 2017/0366353 A1* | 12/2017 | Struttmann | G06F 21/64 | |
| 2018/0060496 A1* | 3/2018 | Bulleit | H04L 9/3268 | |
| 2018/0117447 A1* | 5/2018 | Tran | A63B 71/145 | |
| 2018/0315072 A1* | 11/2018 | Rubin | G06Q 20/387 | |
| 2018/0322543 A1* | 11/2018 | Graybill | G16H 40/20 | |
| 2019/0208354 A1* | 7/2019 | Raduchel | H04W 12/06 | |
| 2020/0058020 A1* | 2/2020 | Natarajan | H04L 63/0823 | |
| 2021/0117962 A1* | 4/2021 | Ortiz | G06Q 20/10 | |

FOREIGN PATENT DOCUMENTS

| | | |
|---|---|---|
| KR | 101591244 B1 | 2/2016 |
| KR | 1020170099155 A | 8/2017 |
| KR | 1020180014534 A | 2/2018 |

* cited by examiner

FIG. 4

| | General users | Medical providers | Medical researchers |
|---|---|---|---|
| Read/write medical information of their own | Both permitted | Both permitted | Both permitted |
| Read medical information of other users | • Basically not permitted, but permitted with approval from account holders (setup for family accounts or the like). | • A part of the information may be viewed without approval in special situations such as an emergency<br>• Basically permitted only with approval from account holders. It is indicated that read requests have been made by medical providers. | • Permitted only with approval from account holders.<br>It is indicated that requests have been made by medical researchers when records of other users are requested. |
| Write medical information of other users | • Basically not permitted, but permitted with approval from account holders (setup for family accounts or the like).<br>• It is indicated that non-medical practitioners have created records. | • Permitted only with approval from account holders.<br>It is indicated that medical providers have created records. | • Basically not permitted, but permitted with approval from account holders.<br>• It is indicated that non-medical practitioners have created records. |

METHOD AND SYSTEM FOR MANAGING MEDICAL INFORMATION PLATFORM BY USING BLOCKCHAIN, AND NON-TRANSITORY COMPUTER-READABLE RECORDING MEDIUM

CROSS-REFERENCE TO RELATED APPLICATION(S)

This application is a national phase of Patent Cooperation Treaty (PCT) International Application No. PCT/KR2018/004217 filed on Apr. 10, 2018. The entire content of PCT International Application No. PCT/KR2018/004217 is hereby incorporated by reference.

FIELD OF THE INVENTION

The present invention relates to a method, system, and non-transitory computer-readable recording medium for managing a medical information platform using a blockchain.

BACKGROUND

Conventionally, medical information is centrally managed by individual medical institutions that treat patients, and it is not allowed in principle to share the medical information outside of the medical institutions, except when the patients request their own medical records. Such a medical information system centered on individual medical institutions results in fragmentation of the medical information of the patients, which makes it difficult to utilize the medical information and deteriorates quality of medical services.

Demand for sharing of medical information has been constantly made by medical community, medical industry, patients, and the like. Although various projects for the medical information sharing have been ongoing for a long time, no clear solution has been presented. Examples thereof include the Blue Button Connector by the United States government, mobile health applications by Apple, and health applications by Samsung Electronics. Although various services other than the foregoing have been presented, the health care services so far have not fulfilled the requirements of an ideal medical information system such as security, reliability, and openness, and have consequently failed to draw active participation of medical consumers, medical providers, and healthcare related organizations or companies.

Medical information platforms using blockchain technology capable of ensuring reliability and transparency have emerged in recent years and attracted attention from many people. Multiple parties with different interests such as medical researchers, medical providers (e.g., hospitals, doctors), and general users (e.g., patients) coexist on such a platform, and the platform is not centered on any one party but based on decentralization. Thus, in order to continuously develop and maintain the platform, methods of managing and operating the platform are more important than anything else.

However, it has been difficult in the prior art to identify whether a user who handles sensitive personal information such as medical information on a decentralized medical information platform is truly reliable. Further, although active participation of users is essential for smooth operation of such a platform, conventional methods of rewarding with tokens or giving commissions performed on various platforms have been insufficient to draw active participation of the users.

In this connection, the inventor(s) present a technique capable of continuously developing and maintaining a medical information platform using blockchain technology, by issuing and operating not only tokens but also points that may be exchanged for the tokens on the medical information platform, giving the points according to extents of contributions to the medical information platform to draw active participation of users and to directly or indirectly judge the reliability of users who handle sensitive personal information such as medical information on the basis of the points, and dynamically calculating a ratio at which the tokens and points are exchanged for each other.

SUMMARY OF THE INVENTION

One object of the present invention is to solve all the above-described problems in the prior art.

Another object of the invention is to create a sustainable and wholesome medical information platform by dynamically calculating a ratio at which tokens and points are exchanged for each other on the medical information platform.

Yet another object of the invention is to draw active participation of users in a medical information platform by giving points according to extents of contributions to the platform.

Still another object of the invention is to directly or indirectly judge the reliability of users who handle sensitive personal information such as medical information on a medical information platform on the basis of points.

The representative configurations of the invention to achieve the above objects are described below.

According to one aspect of the invention, there is provided a method for managing a medical information platform using a blockchain, the method comprising the steps of: dynamically calculating an exchange ratio between tokens and points, with reference to at least one of an amount of points that a user intends to exchange for tokens on a medical information platform, an amount of tokens that the user intends to exchange for points on the medical information platform, an amount of tokens present in a token pool managed by the medical information platform, and an amount of points previously exchanged for tokens on the medical information platform; and providing the user with the tokens or points exchanged with reference to the calculated exchange ratio.

According to another aspect of the invention, there is provided a system for managing a medical information platform using a blockchain, the system comprising: an exchange ratio management unit configured to dynamically calculate an exchange ratio between tokens and points, with reference to at least one of an amount of points that a user intends to exchange for tokens on a medical information platform, an amount of tokens that the user intends to exchange for points on the medical information platform, an amount of tokens present in a token pool managed by the medical information platform, and an amount of points previously exchanged for tokens on the medical information platform; and a token/point provision unit configured to provide the user with the tokens or points exchanged with reference to the calculated exchange ratio.

In addition, there are further provided other methods and systems to implement the invention, as well as non-transitory computer-readable recording media having stored thereon computer programs for executing the methods.

According to the invention, it is possible to create a sustainable and wholesome medical information platform by dynamically calculating a ratio at which tokens and points are exchanged for each other on the medical information platform.

According to the invention, it is possible to draw active participation of users in a medical information platform by giving points according to extents of contributions to the platform.

According to the invention, it is possible to directly or indirectly judge the reliability of users who handle sensitive personal information such as medical information on a medical information platform on the basis of points.

BRIEF DESCRIPTION OF THE DRAWINGS

FIG. 4 illustratively shows the internal configurations of a medical information platform according to one embodiment of the invention.

DETAILED DESCRIPTION OF THE INVENTION

Figure 1:
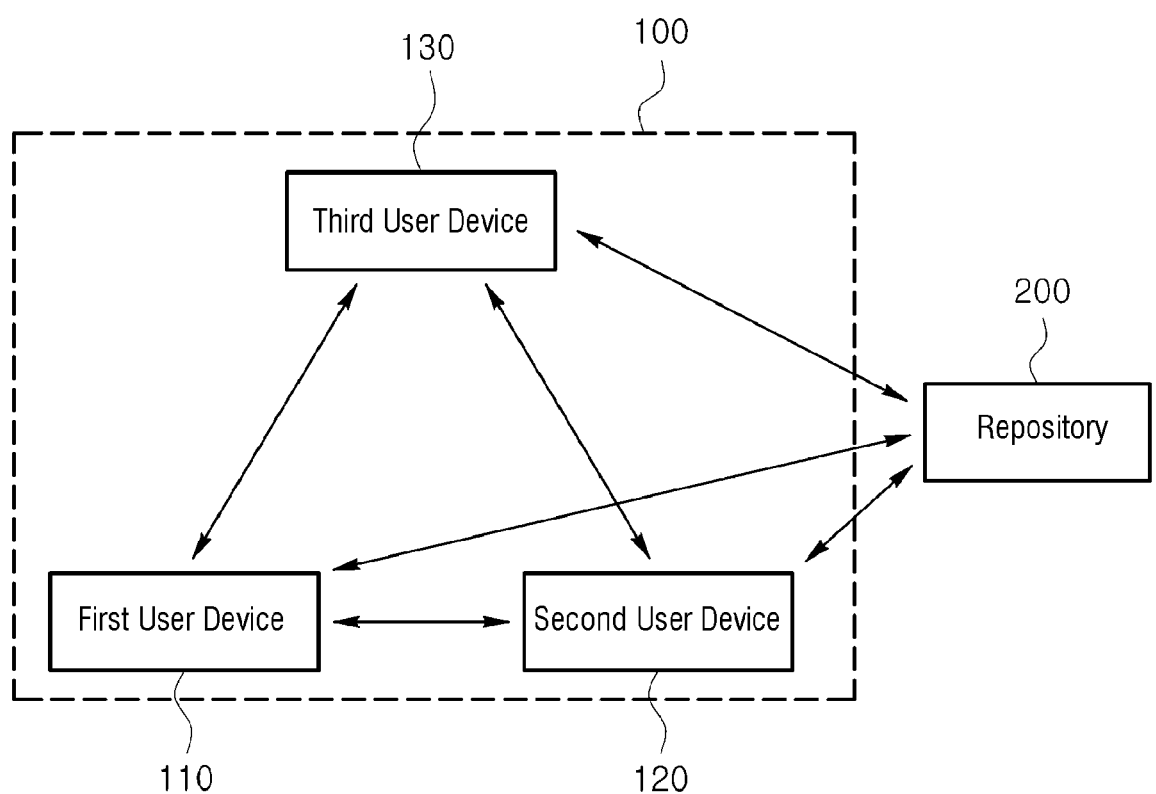
FIG. 1 schematically shows the configuration of an entire system for managing a medical information platform using a blockchain according to one embodiment of the invention.

In the following detailed description of the present invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures and characteristics described herein may be implemented as modified from one embodiment to another without departing from the spirit and scope of the invention. Furthermore, it shall be understood that the locations or arrangements of individual elements within each embodiment may also be modified without departing from the spirit and scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, various preferred embodiments of the present invention will be described in detail with reference to the accompanying drawings to enable those skilled in the art to easily implement the invention.

Configuration of the Entire System

FIG. 1 schematically shows the configuration of the entire system for managing a medical information platform using a blockchain according to one embodiment of the invention.

As shown in FIG. 1, the entire system according to one embodiment of the invention may comprise a communication network, a plurality of user devices 100, and a repository 200.

First, the communication network according to one embodiment of the invention may be configured regardless of communication modality such as wired and wireless communications, and may be constructed from a variety of communication networks such as local area networks (LANs), metropolitan area networks (MANs), and wide area networks (WANs). Preferably, the communication network described herein may be the Internet or the World Wide Web (WWW). However, the communication network is not necessarily limited thereto, and may at least partially include known wired/wireless data communication networks, known telephone networks, or known wired/wireless television communication networks.

For example, the communication network may be a wireless data communication network, at least a part of which may be implemented with a conventional communication scheme such as radio frequency (RF) communication, WiFi communication, cellular communication (e.g., Long Term Evolution (LTE) communication), Bluetooth communication (more specifically, Bluetooth Low Energy (BLE) communication), infrared communication, and ultrasonic communication.

Next, the plurality of devices 100 according to one embodiment of the invention are digital equipment that may function to communicate with each other via the communication network, and any type of digital equipment having a memory means and a microprocessor for computing capabilities, such as a computer, a laptop, a smart phone, and a tablet PC, may be adopted as the plurality of devices 100 according to the invention.

Meanwhile, the plurality of devices 100 according to one embodiment of the invention may include an operating system (to be described below) for managing a medical information platform using a blockchain according to the invention, in the form of a program module such as an application or a widget. Further, the program module may be downloaded from an external application distribution server (not shown), an external system (not shown), or the like.

The medical information platform according to one embodiment of the invention may refer to a decentralized platform capable of sharing encrypted medical information among a plurality of users on the basis of blockchain technology.

Meanwhile, according to one embodiment of the invention, the medical information platform may operate based on a known blockchain (e.g., Bitcoin, Ethereum, or Quantum).

In addition, according to one embodiment of the invention, the blockchain based on which the medical information platform operates may encompass various types of blockchains such as a private blockchain, a public blockchain, or a combination of private and public blockchains.

Further, the medical information platform according to one embodiment of the invention may issue tokens for platform operation or the like. For example, according to one embodiment of the invention, the tokens may be generated on the basis of the conventional Ethereum token standard (i.e., ERC-20) or Quantum token standard (i.e., QRC, a Quantum's counterpart of ERC-20).

Furthermore, the medical information platform according to one embodiment of the invention may include a token pool for integrated management of tokens.

For example, according to one embodiment of the invention, the token pool may include (1) newly issued tokens (for example, after an initial coin offering (ICO) on the medical information platform, the inflation rate applied to the newly issued tokens may be set to be 5% in the first year and to decrease by 30% from the following year), (2) tokens that users pay for using services provided by the medical information platform, and (3) tokens that users exchange for points through the operating system according to the invention.

Meanwhile, according to one embodiment of the invention, the tokens included in the token pool may be used as tokens for which users exchange points through the operating system according to the invention, and may be used to pay for operation, maintenance, and the like of the medical information platform.

Further, the medical information platform according to one embodiment of the invention may further issue points that may be exchanged with tokens, and these points may be used as indicators of extents of users' contributions to the platform. That is, according to one embodiment of the invention, on the medical information platform, predetermined points may be given as a reward to a user who is determined to perform a certain activity meaningful to the platform, on the basis of the extent of the user's contribution.

According to one embodiment of the invention, the above points may be given at every predetermined period (e.g., one month) and may be expired after a predetermined period (e.g., 24 months) from when they are given. Through the foregoing, unnecessary inflation due to unused points may be prevented and the medical information platform may remain healthy.

Further, according to one embodiment of the invention, the points given as above may be set to be exchanged for the tokens after a predetermined reserve period (e.g., three months).

Meanwhile, according to one embodiment of the invention, on the medical information platform, tokens may be set to be traded with other users while points may be set not to be traded with other users. That is, according to one embodiment of the invention, points may not be acquired through trade with other users unlike tokens, and may be set to be acquired by contributing to the platform or paying the platform a large amount of tokens to be exchanged for points. Accordingly, in trading sensitive medical information with other parties including medical institutions or healthcare companies, points may at least serve as an objective indicator that may be used to judge the reliability of the trading parties.

Next, the operating system according to one embodiment of the invention may function to dynamically calculate an exchange ratio between tokens and points, with reference to at least one of an amount of points that a user intends to exchange for tokens on a medical information platform, an amount of tokens that the user intends to exchange for points on the medical information platform, an amount of tokens present in a token pool managed by the medical information platform, and an amount of points previously exchanged for tokens on the medical information platform, and to provide the user with the tokens or points exchanged with reference to the calculated exchange ratio.

The configurations and functions of the operating system according to the invention will be discussed in more detail below. Meanwhile, although the operating system has been described as above, the above description is illustrative and it will be apparent to those skilled in the art that at least a part of the functions or components required for the operating system may be implemented or included in the plurality of devices 100 (e.g., a first user device 110, a second user device 120, and a third user device 130) or an external system (not shown), as necessary. For example, according to one embodiment of the invention, a user may exchange tokens and points according to the invention by installing an application including at least a part of the functions of the operating system (or medical information platform) according to the invention on his/her device, or connecting to a website providing at least at least a part of the functions of the operating system (or medical information platform) according to the invention using his/her device.

Next, the repository 200 according to one embodiment of the invention may be connected with the medical information platform via the communication network, and may function to encrypt and store medical information. For example, according to one embodiment of the invention, the repository 200 may encrypt and store medical information through a private key that may be decrypted only by a user corresponding to the medical information, and a corresponding hash value may be stored on the blockchain.

Meanwhile, the repository 200 according to one embodiment of the invention may be a decentralized repository configured on the basis of interplanetary file system (IPFS).

Configuration of the Operating System

Hereinafter, the functions of the respective components of the operating system crucial for implementing the invention will be discussed.

The operating system according to one embodiment of the invention may comprise an exchange ratio management unit and a token/point provision unit. According to one embodiment of the invention, at least some of the exchange ratio management unit and the token/point provision unit may be program modules to communicate with an external system. The program modules may be included in the operating system in the form of operating systems, application program modules, and other program modules, while they may be physically stored in a variety of commonly known storage devices. Further, the program modules may also be stored in a remote storage device that may communicate with the operating system. Meanwhile, such program modules may include, but not limited to, routines, subroutines, programs, objects, components, data structures, and the like for performing specific tasks or executing specific abstract data types as will be described below in accordance with the invention.

First, the exchange ratio management unit according to one embodiment of the invention may function to dynamically calculate an exchange ratio between tokens and points, with reference to at least one of an amount of points that a user intends to exchange for tokens on a medical information platform, an amount of tokens that the user intends to exchange for points on the medical information platform, an amount of tokens present in a token pool managed by the medical information platform, and an amount of points previously exchanged for tokens on the medical information platform.

Specifically, when a user intends to exchange at least a part of his/her points for tokens on the medical information platform, the exchange ratio management unit according to one embodiment of the invention may dynamically calculate a token exchange ratio of the points to be exchanged, on the basis of an amount of the points to be exchanged and the amount of tokens present in the token pool.

For example, the exchange ratio management unit according to one embodiment of the invention may calculate a ratio at which points are exchanged for tokens, on the basis of a ratio between a predetermined percentage of the amount of tokens held in the token pool and the amount of points that the user intends to exchange for tokens.

More specifically, the exchange ratio management unit according to one embodiment of the invention may calculate the ratio at which points are exchanged for tokens as a value obtained by dividing 30% of the amount of tokens held in the token pool by the amount of points that the user intends to exchange for tokens.

Further, when the user intends to exchange at least a part of his/her tokens for points, the exchange ratio management unit according to one embodiment of the invention may dynamically calculate a point exchange ratio of the tokens to be exchanged, on the basis of an amount of points previously exchanged for tokens by the user on the medical information platform.

For example, the exchange ratio management unit according to one embodiment of the invention may calculate a ratio at which tokens are exchanged for points, by calculating the amount of points previously exchanged for tokens by the user on the medical information platform, using at least one of a linear function and a logarithmic function.

More specifically, the exchange ratio management unit according to one embodiment of the invention may calculate the ratio at which tokens are exchanged for points, by calculating the amount of points previously exchanged for tokens on the medical information platform, using a linear function when the amount is not greater than a predetermined level, and using a logarithmic function when the amount is greater than the predetermined level.

Next, the token/point provision unit according to one embodiment of the invention may function to provide the user with the tokens or points exchanged with reference to the calculated exchange ratio between tokens and points.

Figure 2:
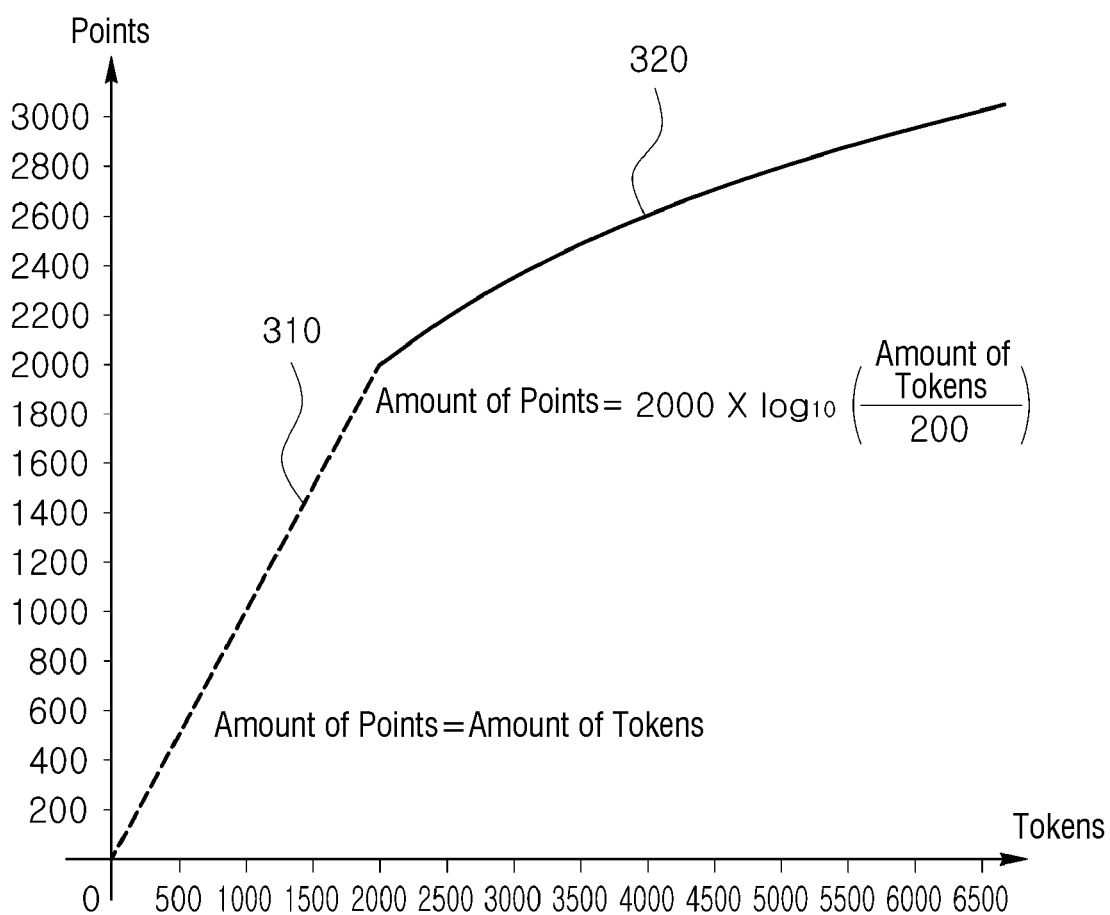
FIG. 2 illustratively shows how to calculate an exchange ratio between tokens and points according to one embodiment of the invention.

FIG. 2 illustratively shows how to calculate an exchange ratio between tokens and points according to one embodiment of the invention.

Referring to FIG. 2, the operating system according to one embodiment of the invention may calculate a point exchange ratio of tokens as 1:1 until an amount of points previously exchanged for tokens by a user reaches 2,000 (310), and may calculate the point exchange ratio of tokens such that an amount of exchanged points is $2,000 \times \log_{10}$ (amount of tokens/200) when the amount of points previously exchanged for tokens by the user is greater than 2,000.

That is, according to one embodiment of the invention, users may acquire basic points by exchanging the same amount of tokens, but should use a large amount of tokens in order to acquire more points, so that the users are induced to acquire points through certain meaningful activities (i.e., contributions) on the platform.

Meanwhile, the formula for calculating the ratio at which tokens are exchanged for points according to the invention is not necessarily limited to the foregoing, and may be changed to various formulas as long as the objects of the invention may be achieved.

Figure 3:
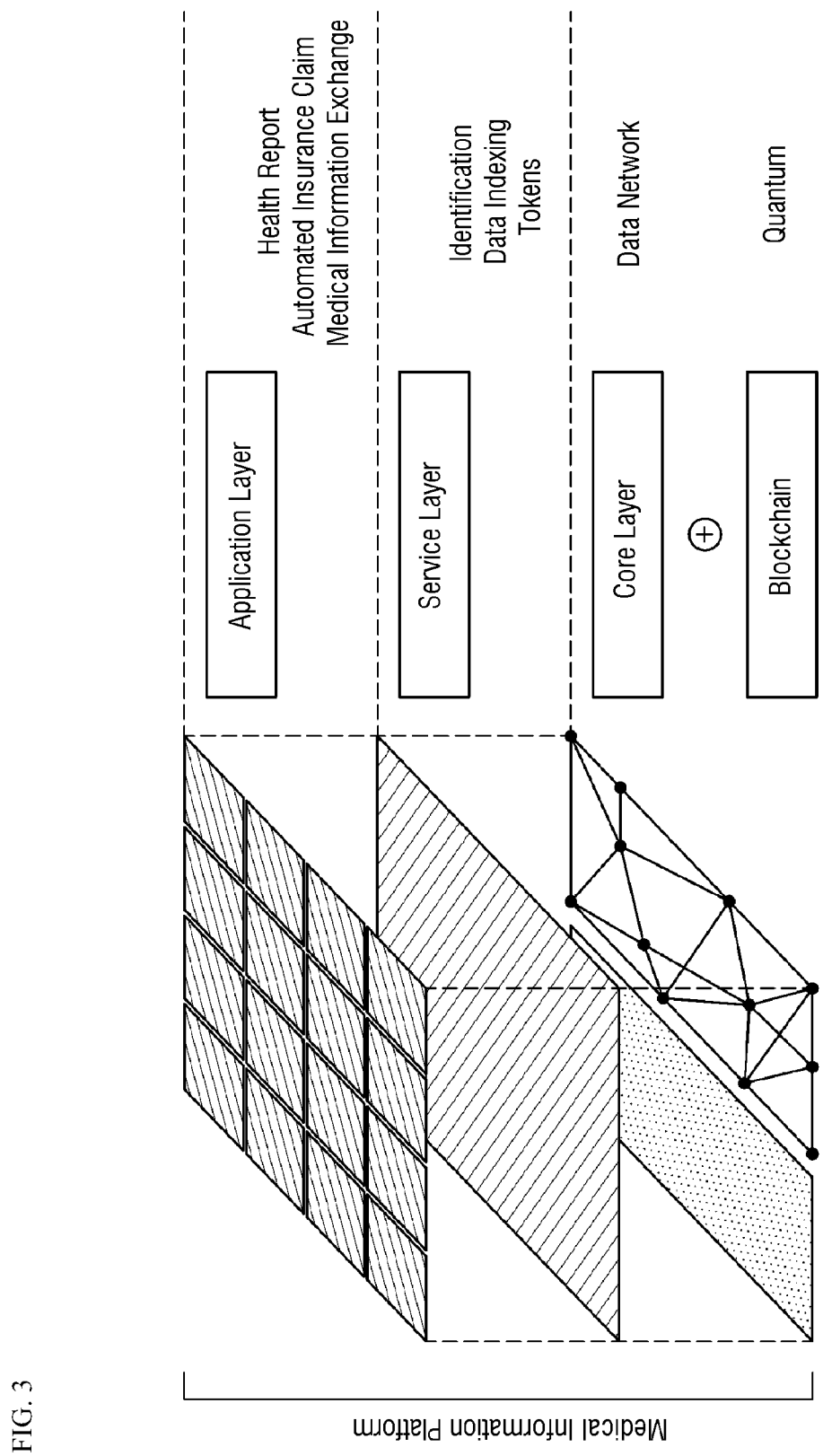
FIG. 3 illustratively shows the internal configurations of a medical information platform according to one embodiment of the invention.

FIGS. 3 and 4 illustratively show the internal configurations of a medical information platform according to one embodiment of the invention.

First, referring to FIG. 3, the medical information platform according to one embodiment of the invention may comprise a core layer, a service layer, and an application layer, and may operate based on a Quantum blockchain among conventional blockchains.

The core layer according to one embodiment of the invention may function as a distributed database that may safely protect medical information of users using encryption technology (e.g., by encrypting the medical information through private keys that may be decrypted only by the users corresponding to the medical information). Further, a separate storage space may be required in order to store or manage the medical information of the users since the amount of information that may be stored in the blockchain is limited, and the core layer may function to manage the repository 200 to this end.

Meanwhile, according to one embodiment of the invention, the medical information of the users provided to the core layer through the application layer may be encrypted by the application layer.

Further, the service layer according to one embodiment of the invention may enable the application layer and the core layer to be connected to each other, and may function to manage user information (e.g., user accounts for identifying the users), index the medical information, and so on. Furthermore, the service layer according to one embodiment of the invention may be connected to the core layer through the medical information stored on the blockchain (e.g., the medical information may be stored in the repository 200 when it is large and a corresponding hash value may be stored on the blockchain, wherein the service layer may find from the core layer a location where the medical information corresponding to the hash value is stored), and may function to input/output the medical information to/from the core layer.

Meanwhile, the service layer according to one embodiment of the invention may comprise a smart contract part based on an Ethereum virtual machine (EVM) (e.g., a smart contract may include information on a user's account, information on a link related to a location where the medical information is stored, and the like) and a part connecting the application layer and the core layer.

Further, the application layer according to one embodiment of the invention may include various types of application programs running on the user devices 100 to manage the medical information platform.

Referring to FIG. 4, permission for encrypted medical information (e.g., permission to read or write the medical information) may be set on the medical information platform, on the basis of types of users who use the platform.

For example, according to one embodiment of the invention, the types of the users may include general users, medical providers, and medical researchers. According to one embodiment of the invention, the general users, the medical providers, and the medical researchers may all be granted permission to read or write the medical information of their own, and permission to read or write the medical information of other users may be basically set such that the medical information cannot be accessed without separate approval from the other users. However, according to one embodiment of the invention, the medical providers may be temporarily granted permission to read a part of the medical information of other users, in predetermined situations such as an emergency. Meanwhile, the medical providers and the medical researchers may be granted permission to request other users to grant permission to read the medical information of the other users.

Meanwhile, according to one embodiment of the invention, at least one of a conventional centralized method to get direct authentication from a trusted organization and a peer-to-peer (P2P) method to get authentication from an authenticated user may be used to classify the types of the users on the medical information platform.

According to one embodiment of the invention, the P2P authentication method may be determined by voting of a plurality of authenticated users (in this case, voting results of individual users may not be revealed through an anonymous indorsement protocol (AIP) using a zero-knowledge proof method defined by Indorse, for example). Further, according to one embodiment of the invention, in order to increase the reliability of the P2P authentication method, predetermined points may be paid to an authenticated user participating in an authentication process of another user, in the form of a deposit (or collateral). The points paid in the form of the deposit may be confiscated from (or predetermined points or tokens may be imposed as a fine to) any user who is judged to be malicious or undermine trust of the authentication process, while predetermined points may be given as a reward to any user who is judged to perform the authentication process in good faith or in a normal manner.

The embodiments according to the invention as described above may be implemented in the form of program instructions that can be executed by various computer components, and may be stored on a computer-readable recording medium. The computer-readable recording medium may include program instructions, data files, data structures and the like, separately or in combination. The program instructions stored on the computer-readable recording medium may be specially designed and configured for the present invention, or may also be known and available to those skilled in the computer software field. Examples of the computer-readable recording medium include the following: magnetic media such as hard disks, floppy disks and magnetic tapes; optical media such as compact disk-read only memory (CD-ROM) and digital versatile disks (DVDs); magneto-optical media such as floptical disks; and hardware devices such as read-only memory (ROM), random access memory (RAM) and flash memory, which are specially configured to store and execute program instructions. Examples of the program instructions include not only machine language codes created by a compiler or the like, but also high-level language codes that can be executed by a computer using an interpreter or the like. The above hardware devices may be configured to operate as one or more software modules to perform the processes of the present invention, and vice versa.

Although the present invention has been described above in terms of specific items such as detailed elements as well as the limited embodiments and the drawings, they are only provided to help more general understanding of the invention, and the present invention is not limited to the above embodiments. It will be appreciated by those skilled in the art to which the present invention pertains that various modifications and changes may be made from the above description.

Therefore, the spirit of the present invention shall not be limited to the above-described embodiments, and the entire scope of the appended claims and their equivalents will fall within the scope and spirit of the invention.

What is claimed is:

1. A method performed in a system for managing a medical information platform using a blockchain, the method comprising the steps of:
by a processor of a device, operating the medical information platform comprising a core layer, a service layer, and an application layer based on the blockchain, wherein the service layer comprises a smart contract part for issuing tokens;
by the processor of the device, dynamically calculating an exchange ratio between tokens associated with the blockchain and points, with reference to at least one of an amount of points that a user intends to exchange for tokens on the medical information platform, an amount of tokens that the user intends to exchange for points on the medical information platform, an amount of tokens present in a token pool managed by the medical information platform, and an amount of points previously exchanged for tokens on the medical information platform; and
by the processor of the device, providing the user with the tokens or points exchanged with reference to the calculated exchange ratio,
wherein a ratio at which tokens are exchanged for points is calculated using a linear function when the amount of points previously exchanged for tokens on the medical information platform is not greater than a predetermined level, and using a logarithmic function when the amount of points previously exchanged for tokens on the medical information platform is greater than the predetermined level, and
wherein the device communicates with a repository;
the processor instructs the application layer to encrypt medical information of each of a plurality of users through private keys;
the processor stores the encrypted medical information in the repository and stores a hash value corresponding to the encrypted medical information in the blockchain;
the processor connects the service layer to the core layer through the hash value stored in the blockchain; and
the processor instructs the service layer to find from the core layer a location where the encrypted medical information corresponding to the hash value is stored.

2. The method of claim 1, wherein in the calculating step, when the user intends to exchange at least a part of the user's points for tokens on the medical information platform, a token exchange ratio of the points to be exchanged is dynamically calculated on the basis of an amount of the points to be exchanged and the amount of tokens present in the token pool, and when the user intends to exchange at least a part of the user's tokens for points, a point exchange ratio of the tokens to be exchanged is dynamically calculated on the basis of an amount of points previously exchanged for tokens by the user on the medical information platform.

3. The method of claim 1, wherein points are given as a reward to the user on the basis of an extent of the user's contribution to the medical information platform.

4. The method of claim 3, wherein the points are given at every predetermined period and expired after a predetermined period from when the points are given.

5. The method of claim 3, wherein the given points are capable of being exchanged for the tokens after a predetermined reserve period.

6. The method of claim 1, wherein the user's points are capable of being used as a collateral for the user's participation in peer-to-peer authentication associated with the medical information platform.

7. The method of claim 1, wherein a ratio at which points are exchanged for tokens is calculated on the basis of a ratio between a predetermined percentage of the amount of tokens present in the token pool and the amount of points that the user intends to exchange for tokens.

8. The method of claim 1, wherein tokens are issued on the medical information platform on the basis of an Ethereum token standard (ERC-20) or a Quantum token standard (QRC).

9. A non-transitory computer-readable recording medium having stored thereon a computer program for executing the method of claim 1.

10. A system for managing a medical information platform using a blockchain, the system comprising:
the medical information platform comprising a core layer, a service layer, and an application layer operated based on the blockchain, wherein the service layer comprises a smart contract part for issuing tokens;

a device comprising a processor to:

dynamically calculate an exchange ratio between tokens and points, with reference to at least one of an amount of points that a user intends to exchange for tokens associated with the blockchain on the medical information platform, an amount of tokens that the user intends to exchange for points on the medical information platform, an amount of tokens present in a token pool managed by the medical information platform, and an amount of points previously exchanged for tokens on the medical information platform; and provide the user with the tokens or points exchanged with reference to the calculated exchange ratio, wherein a ratio at which tokens are exchanged for points is calculated using a linear function when the amount of points previously exchanged for tokens on the medical information platform is not greater than a predetermined level, and using a logarithmic function when the amount of points previously exchanged for tokens on the medical information platform is greater than the predetermined level, and wherein the device communicates with a repository;

the processor instructs the application layer to encrypt medical information of each of a plurality of users through private keys;

the processor stores the encrypted medical information in the repository and stores a hash value corresponding to the encrypted medical information in the blockchain;

the processor connects the service layer to the core layer through the hash value stored in the blockchain; and the processor instructs the service layer to find from the core layer a location where the encrypted medical information corresponding to the hash value is stored.

11. The method of claim 1, wherein the smart contract part is based on an Ethereum virtual machine (EVM).

* * * * *